United States Patent [19]

Woods et al.

[11] 4,232,446
[45] Nov. 11, 1980

[54] GAGE FOR MEASURING DECREASE IN DIMENSION OF TEST SPECIMEN IN TENSILE TEST

[75] Inventors: Don F. Woods, North Ogden; Ronald F. Larsen, Willard, both of Utah

[73] Assignee: The United States of America as represented by the Secretary of the Air Force, Washington, D.C.

[21] Appl. No.: 25,412

[22] Filed: Mar. 30, 1979

[51] Int. Cl.³ .......................... G01B 3/20; G01B 7/06
[52] U.S. Cl. ............................ 33/143 L; 33/DIG. 11; 73/860
[58] Field of Search .............. 33/143 R, 143F, 143 L, 33/147 R, 147 D, 147 N, 172 E, DIG. 11; 73/781, 788, 855, 860

[56] References Cited

U.S. PATENT DOCUMENTS

| 3,142,907 | 8/1964 | Reef ................................ 33/147 R |
| 3,238,626 | 3/1966 | White ............................. 33/143 R |
| 3,895,446 | 7/1975 | Orlov et al. ................... 33/174 L |
| 3,950,855 | 4/1976 | Peonski ......................... 33/143 L |

FOREIGN PATENT DOCUMENTS 103015  5/1899  Fed. Rep. of Germany ......... 33/143 F

*Primary Examiner*—Richard R. Stearns
*Attorney, Agent, or Firm*—Joseph E. Rusz; Casimer K. Salys

[57] ABSTRACT

A test gage for measuring the decrease in one dimension of a test specimen having a frame member with a sliding member positioned within the frame member. The test apparatus is adapted to receive a test specimen between the sliding member and one side of the frame member. The sliding member is held in contact with the test specimen by a spring. A proximity measuring device senses the position of the sliding member with respect to the frame member and provides an output signal proportional to displacement. Elastic bands are used to support the test gage on a tensile test machine which is used to apply a stress to the test specimen.

1 Claim, 3 Drawing Figures

GAGE FOR MEASURING DECREASE IN DIMENSION OF TEST SPECIMEN IN TENSILE TEST

RIGHTS OF THE GOVERNMENT

The invention described herein may be manufactured and used by or for the Government of the United States for all governmental purposes without the payment of any royalty.

BACKGROUND OF THE INVENTION

This invention relates to apparatus for obtaining data from a test specimen to determine Poisson's ratio for the test specimen.

Extensometers have been used for measuring the decrease in width when a sample is elongated in a tensile test machine. These cannot be used where attachment to the sample results in damage to the sample which can result in premature rupture of the sample and in other ways affect the test results.

In testing soft materials such as solid rocket propellant gas dilatometers have been used wherein changes in the total volume of the material is determined by a change in pressure within a chamber. These systems are costly and difficult to use and the system is highly sensitive to temperature change. Liquid dilatometers are less temperature sensitive but it must have the liquid circulated for temperature control and is not easy to use. Also these cannot be used where the liquid will have an adverse effect on the test sample.

BRIEF SUMMARY OF THE INVENTION

According to this invention, a gage is provided which fits around a test specimen. The gage includes a spring loaded sliding member positioned within a frame member. The sliding member follows the test specimen as it decreases in width during elongation in a tensile test machine. A proximity detecting device senses the position of the sliding member with respect to the frame member and provides an electrical output signal proportional to displacement which may be supplied to a computer together with other test data for determining Poisson's ratio. The gage is supported on the tensile test machine with flexible attachments.

IN THE DRAWINGS

DETAILED DESCRIPTION OF THE INVENTION

Figure 1:
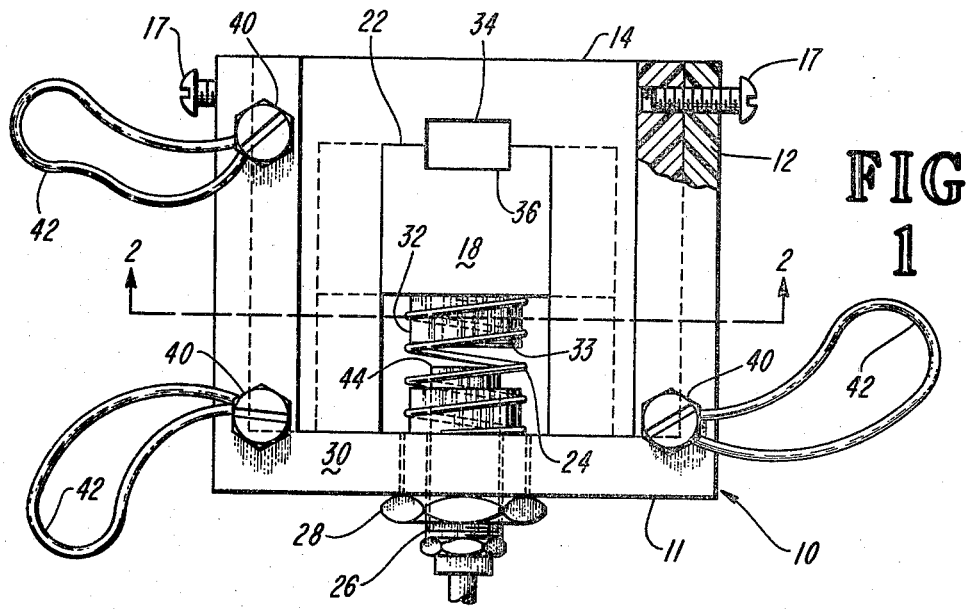
FIG. 1 is a partially schematic view of a test sample width measuring gage according to the invention.
Figure 2:
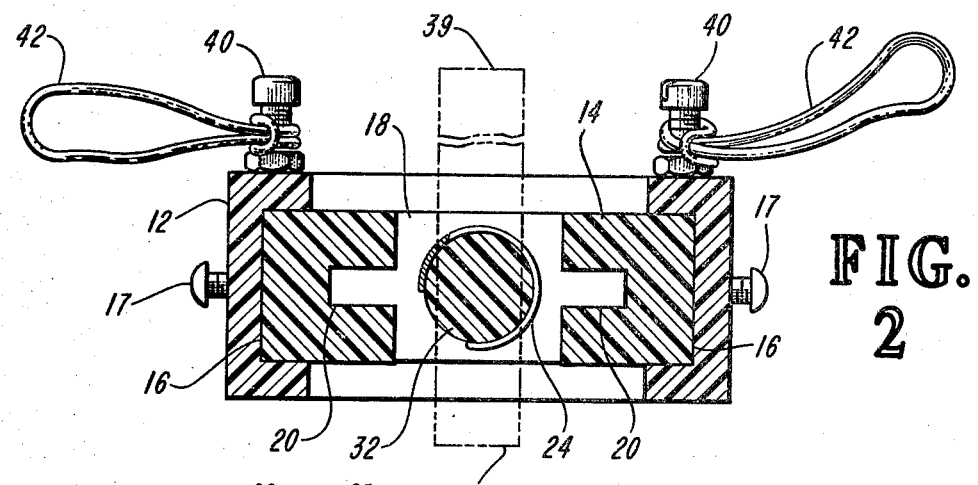
FIG. 2 is a partially schematic sectional view of the device of FIG. 1 taken along the lines 2—2.

Reference is now made to FIG. 1 of the drawing which shows a gage 10 including a frame member 11 with an outer member 12 and an inner member 14. The member 14 fits into slots 16 in member 12 and is secured by two screws 17. A slidable member 18 fits into slots 20 in member 14. The slidable member 18 is urged toward side 22 of member 14 by a spring 24. A proximity detector 26 is threaded into a bushing 28 which is threaded into side 30 of frame member 12. The spring 24 is held in place by bushing 28 and a boss member 32 on slidable member 18. An aluminum disc 33 is cemented to the end of boss member 32 to provide target for the proximity detector 26.

Figure 3:
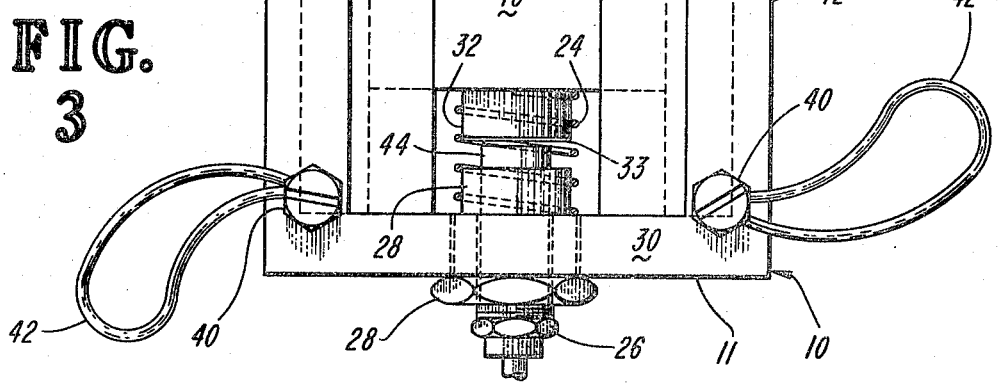
FIG. 3 is a partially schematic view of the device of FIG. 1 with a test sample in place.

Notches 34 and 36 are provided in members 14 and 18 for engaging a test specimen 39, as shown in FIG. 3. Four screws 40 are threaded into member 12 to provide support for the gage 10. Elastic bands 42 are secured to screws 40 and are attached to the tensile test apparatus, not shown, to provide support for the gage when the test sample is gripped by the tensile test apparatus. Means, other than elastic bands 42, may be provided for supporting the gage 10, such as soft springs.

In the device constructed, the parts 12, 14, 18 and 28 were made of polytetrafluoroethylene; however, any low friction material could be used. Also, other light weight materials could be used with low friction material being provided on the adjoining sliding surfaces of parts 14 and 18. The proximity detector used was a Multi-Vit Displacement Measuring Device Model KD 2300-25 with a P-3100 power supply made by Kaman Scientific Corporation.

In the operation of the device, the test specimen 39 is positioned in notches 34 and 36 and the test specimen is then connected to the tensile test apparatus with the gage being supported on the tensile test apparatus by elastic bands 42. In tests made, a propellant test specimen and gage were positioned in an environmental pressure/temperature chamber, not shown, with a pressure of 600 psig and a temperature of $-30°$ F. Selected for the test.

As the test specimen is stretched and the dimension perpendicular to the applied stress decreases, the continuous decrease in dimension is followed by the slidable member 18. The proximity detector 26 continuously senses the spacing between the sensing head 44, of the proximity detector 26, and the aluminum target 33 and provides an electrical output signal which may be supplied to a computer with other test data for determining Poisson's ratio.

Since the spring 24 applies a pinching of the propellant, the measurements below 10 percent elongation of the sample are not accurate; however, there is very little change in volume below 10 percent elongation so that the slight pinching is not important, since it does not materially effect the results in the important part of the test beyond 10 percent elongation.

The output data from the device of the invention has been found comparable with data obtained with much more costly and elaborate equipment.

There is thus provided a simple low cost system for measuring the decrease in width of a test sample in a tensile test machine, for use in determining Poisson's ratio, which does not have some of the disadvantages of prior art apparatus.

We claim:

1. A device for measuring the decrease in one dimension of a compression sensitive test specimen in a direction perpendicular to the applied stress in a tensile test machine, comprising:
    a polytetrafluoroethylene frame member;
    a polytetrafluoroethylene slidable member positioned in said frame member;
    a means for providing a low friction bearing between said slidable member and said frame member;
    notches in said slidable and frame members, for receiving a test specimen therebetween;
    a spring positioned between the frame member and the slidable member, on the side of said slidable member remote from said notches; and
    a proximity measuring device secured to said frame member and a metallic target secured to the slidable member.

* * * * *